United States Patent [19]
Sytkowski et al.

[11] Patent Number: 5,804,382
[45] Date of Patent: Sep. 8, 1998

[54] METHODS FOR IDENTIFYING DIFFERENTIALLY EXPRESSED GENES AND DIFFERENCES BETWEEN GENOMIC NUCLEIC ACID SEQUENCES

[75] Inventors: Arthur J. Sytkowski, Arlington; Meiheng Yang, Boston, both of Mass.

[73] Assignee: Beth Israel Deaconess Medical Center, Inc., Boston, Mass.

[21] Appl. No.: 644,326

[22] Filed: May 10, 1996

[51] Int. Cl.$^6$ .............................. C12Q 1/68; C12P 19/34
[52] U.S. Cl. .............................................. 435/6; 435/91.2
[58] Field of Search .................. 435/6, 91.2; 935/77, 935/78

[56] References Cited

U.S. PATENT DOCUMENTS 5,436,142  7/1995  Wigler et al. ........................... 435/91.2
5,580,726  12/1996  Villeponteau et al. ...................... 435/6

OTHER PUBLICATIONS

Davis, R., et al., "Expression of Single Transfected cDNA Converts Fibroblasts to Myoblasts," *Cell*, vol. 51, 987–1000, (1987);.

Hedrick, S., et al., "Isolation of cDNA Clones Encoding T Cell–specific Membrane–associated Proteins," *Nature*, vol. 308, 149–153 (1984);.

Hubank, M. and Schatz, D.G., "Identifying Differences in mRNA Expression by Representational Difference Analysis of cDNA," *Nucleic Acids Research*, vol. 22, No. 25, 5640–5648 (1994);.

Liang, P. and Pardee, A., "Differential Display of Eukaryotic Messenger RNA by Means of the Polymerase Chain Reaction," *Science*, vol. 257, 967–971 (1992);.

Lisitsyn, N., et al., "Cloning the Differences Between Two Complex Genomes," *Science*, vol. 259, 946–951 (1993);.

Mather, E., et al., "Expression of J Chain RNA in Cell Lines Representing Different Stages of B Lymphocyte Differentiation," *Cell*, vol. 23, 369–378 (1981);.

Sive, H. and St John, T., "A Simple Subtractive Hybridization Technique Employing Photoactivatable Biotin and Phenol Extraction," *Nucleic Acids Research*, vol. 16, No. 22, 10937 (1988);.

Straus, D. and Ausubel, F., "Genomic Substraction for Cloning DNA Corresponding to Deletion Mutations," *Proc. Natl. Acad. Sci. USA*, vol. 87, 1889–1893 (1990);.

Wang, Z. and Brown, D., "A Gene Expression Screen," *Proc. Natl. Acad. Sci. USA*, vol. 88, 11505–11509 (1991);.

Welsh, J. et al., "Arbitrarily Primed PCR Fingerprinting of RNA," *Nucleic Acids Res.*, vol. 20, No. 19, 4965–4970 (1992);.

Wieland, I., et al., "A Method for Difference Cloning: Gene Amplification Following Subtractive Hybridization," *Proc. Natl. Acad. Sci. USA*, vol. 87, 2720–2724 (1990);.

Zeng, J., et al., "Differential cDNA Cloning by Enzymatic Degrading Subtraction (EDS)," *Nucleic Acids Research*, vol. 22, No. 21, 4381–4385 1994).

*Primary Examiner*—Eggerton A. Campbell
*Attorney, Agent, or Firm*—Lahive & Cockfield, LLP

[57] ABSTRACT

Methods for identifying differentially expresses genes and differences between genomic nucleic acid sequences are described. These methods typically include: (a) providing a tester DNA molecule with an amplification tag at the 5' and 3' ends of the molecule and a driver DNA or RNA molecule lacking said amplification tag; (b) hybridizing said tester and said driver molecules to form a reaction mixture, wherein said reaction mixture comprises a tester—tester homoduplex, a tester-driver heteroduplex, a driver—driver homoduplex, a single stranded driver DNA molecule and a single stranded tester DNA molecule; (c) treating said reaction mixture to reduce the number of single stranded molecules in said mixture; (d) treating said reaction mixture to remove said amplification tag from said tester-driver heteroduplex; and (e) amplifying said tester—tester homoduplex from said reaction mixture to form an amplification product, wherein steps (c) and (d) occur before step (e).

34 Claims, 1 Drawing Sheet

5,804,382

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 400 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| GTACCCCTAC | GACGCCGGGA | CGACAGCGGC | TTCACCTTCT | CCTCCCCCAA | CTTCGCCACC | 60 |
| ATCCCGCAGA | CACGGTGACC | GAGATAACGT | CCTCCTCTCC | CAGCCACCCG | GCCAGCTCCT | 120 |
| TCTACTACCC | GCGGCTGAAG | GCCTGCTCCC | ATCGCCAGGG | TGACACTGGT | GCGGCTGCGA | 180 |
| CAGAGCCCCA | GGGCCTTCAT | CCCTCCCGCC | CCAGTCCTGC | CCAGCAGGAC | AATGAGATTG | 240 |
| TAGACAGCGC | CTCAGTTCCA | GAAACGCCGC | TGGACTGCGA | GGTCTCCCTG | TGGTCGTCCT | 300 |
| GGGGACTGTG | CGGAGGCCAC | TGTGGGAGGC | TCGGGTCCAA | GAGCAGGACT | CCGTACGCCC | 360 |
| GGGTCCAGCC | CGCCAACAAC | GGGAGCCCCT | GCCCCGAGCT | | | 400 |

( 2 ) INFORMATION FOR SEQ ID NO:2:

( i ) SEQUENCE CHARACTERISTICS:
        ( A ) LENGTH: 196 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | | | | | |
|---|---|---|---|---|---|---|
| AGCTGCCCCG | AAGTCCGTCC | TTCCTGCAGG | ACCCAACTCC | ACGTAGAGTG | AGTGCAGCCA | 60 |
| CACAGCAGTA | ACCAGATAGA | GCAGCCTCCC | CTGCAGACAT | GAGCGAAGAA | GGGATCCAGA | 120 |
| GAGCCAAGGC | TGTACCATAG | ATTCTTGTGG | GGTCAAAGGG | GCAGGCAGTA | TGTCCCGGCC | 180 |
| CCTCATCCAG | TGGTAC | | | | | 196 |

( 2 ) INFORMATION FOR SEQ ID NO:3:

( i ) SEQUENCE CHARACTERISTICS:
        ( A ) LENGTH: 228 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

| | | | | | | |
|---|---|---|---|---|---|---|
| AGCTCCTTCC | AACTCCTCAG | AACCTCCACT | CTATGGATCT | GGACCTCTGG | ATTCGGCTTT | 60 |
| CTCCCTGGCA | CTGCTTCAGG | AAGACGTTGA | GAATTGACCT | TACACAATCC | CTGCGCCCTC | 120 |
| CTCACAGGAG | CCTTTCACTT | TACAGTGGTA | AGGGGCTGGT | TCTGGAGAAC | TGGCTGATGC | 180 |
| TCTGAATTTC | TTCATATACC | CCACATTTGA | CTTTGGCTTA | CACTGTAC | | 228 |

( 2 ) INFORMATION FOR SEQ ID NO:4:

( i ) SEQUENCE CHARACTERISTICS:
        ( A ) LENGTH: 113 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

| | | | | | | |
|---|---|---|---|---|---|---|
| AGCTGCGAGT | CCTGTGTGAG | TTGGTCACCC | TGACCTTTAA | TCCCTCCACC | CCTGTCCTGG | 60 |
| AAAGATTAGA | CGCTCCTCTG | CACCACTGTG | CTCGGGTGTG | TTGGGTGTCT | TAT | 113 |

( 2 ) INFORMATION FOR SEQ ID NO:5:

( i ) SEQUENCE CHARACTERISTICS:
        ( A ) LENGTH: 93 base pairs

-continued (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

AGCTCCTCTA TCAGCATCTT TGGTGTCTCC CAGTGATCAA CCAGAGAGTG GTTGTGGAGC 60

CTGTTGCCCA GTTGGTTTCA AGCCAGAGAC ATT 93

(2) INFORMATION FOR SEQ ID NO:6:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:6:

ACTCTTGCTT GGACGAGCTC T 21

(2) INFORMATION FOR SEQ ID NO:7:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

ACTGAGAACG AACCTGCTCG AGA 23

METHODS FOR IDENTIFYING DIFFERENTIALLY EXPRESSED GENES AND DIFFERENCES BETWEEN GENOMIC NUCLEIC ACID SEQUENCES

BACKGROUND OF THE INVENTION

One common and fundamental problem of molecular biology confronts scientists when they desire to understand the differences between two similar genomes. One simple form of this problem can occur when a genome becomes deleted for sequences present in another genome due to germ-line mutation, as can happen in genetic disease (Martin (1987) *Science* 238:765–772; Landergren et al. (1988) *Science* 242:229–237), or due to somatic mutations, as can happen during the development of cancer (Ponder (1988) *Nature* 335:400–402; Sager (1989) *Science* 246:1406–1412). Differences in genomes can also be acquired by infection with a DNA-based pathogens. Methods for identifying and isolating sequences present in one DNA population that are absent or reduced in another are called "difference cloning."

The isolation and identification of differentially expressed genes is of great importance in the study of embryogenesis, cell growth and differentiation, and neoplastic transformation. Furthermore, the analysis of the differences between two complex genomes holds promise for the discovery of infectious agents and probes useful for genetic studies. A variety of methods have been employed to achieve this end. They include differential screening of cDNA libraries with selective probes, subtractive hybridization utilizing DNA/DNA hybrids or DNA/RNA hybrids, RNA fingerprinting and differential display (Mather, et al. (1981) *Cell* 23:369–378; Hedrick et al. (1984) *Nature* 308:149–153; Davis et al. (1992) *Cell* 51:987–1000; Welsh et al. (1992) *Nucleic Acids Res.* 20:4965–4970; and Liang and Pardee (1992) *Science* 257:967–971). Recently, PCR-coupled subtractive processes have also been reported (Straus and Ausubel (1990) *Proc. Natl. Sci. USA* 87:1889–1893; Sive and John (1988) *Nucleic Acids Res.* 16:10937; Wieland et al. (1990) *Proc. Natl. Acad. Sci. USA* 87:2720–2724; Wang and Brown (1991) *Proc. Natl. Acad. Sci. USA* 88:11505–11509; Lisitsyn et al. (1993) *Science* 259:946–951; Zeng et al. (1994) *Nucleic Acids Res.* 22:4381–4385; Hubank and Schatz (1994) *Nucleic Acids Res.* 22:5640–5648). Each of these methods has achieved some success but each has some inherent limitations. For example, problems associated with differential display include identification of "false positives," redundancy, and under-representation of certain mRNA species. Liang and Pardee (1992) *Science* 257:967–971. In addition, cDNA-RDA (Hubank and Schatz (1994) *Nucleic Acids Res.* 22:5640–5648; Lisitsyn et al. (1993) *Science* 259:946–951) is a labor-intensive process, and its efficiency remains to be evaluated.

Thus a need still exists to develop a more efficient method for identification of differentially expressed genes and differences in genomic sequences.

Accordingly, an object of the invention is to provide a method for identifying differentially expressed genes and differences between genomic nucleic acid sequences.

Another object of the invention is to provide a differentially expressed nucleic acid isolated by the method of the invention.

A further object of the invention is to provide a kit for identifying a differentially expressed gene or for identifying a difference between genomic nucleic acid sequences.

SUMMARY OF THE INVENTION

The method described herein, termed "Linker Capture Subtraction" (LCS), overcomes many of the problems associated with present methods for identifying differentially expressed genes and differences in genomic sequences. Unlike other methods such as representational difference analysis (RDA) (Hubank and Schatz (1994) *Nucleic Acids Res.* 22:5640–5648; Lisitsyn et al. (1993) *Science* 259:946–951), LCS is a subtraction method coupled to PCR amplification which does not rely on a kinetic mechanism of enrichment of selected sequences. Rather, LCS achieves enrichment by specifically preserving PCR-priming sites of target sequences, using a nuclease which digests single-stranded nucleic acid as the mediator. Moreover, LCS is also a less labor-intensive process. Thus, the invention pertains to novel methods for identifying and isolating differentially expressed genes as well as to novel methods for identifying differences between genomic DNA sequences.

The invention features a method for identifying a differentially expressed gene. The method includes (a) providing a tester DNA molecule with an amplification tag at the 5' and 3' ends of the molecule and a driver DNA or RNA molecule lacking the amplification tag, (b) hybridizing the tester and the driver molecules to form a reaction mixture, wherein the reaction mixture comprises a tester—tester homoduplex, a tester-driver heteroduplex, a driver—driver homoduplex, a single stranded driver DNA molecule and a single stranded tester DNA molecule, (c) treating the reaction mixture to reduce the number of single-stranded molecules in the mixture, (d) treating the reaction mixture to remove the amplification tag from the tester-driver heteroduplex, and (e) amplifying the tester—tester homoduplex from the reaction mixture to form an amplification product, wherein steps (c) and (d) occur before step (e).

In one embodiment, the tester DNA molecule is isolated from a cell which is exposed to conditions in vivo or in vitro which alter gene expression, e.g., a cancer cell, a virally infected cell, a cell exposed to selected chemical substances, a cell exposed to radiation, a cell exposed to different nutrient conditions, a cell exposed to selected factors (e.g., hormone or growth factors), and the driver DNA molecule is isolated from a normal cell. In one embodiment, the tester DNA molecule is isolated from a highly malignant cancer cell, e.g., a PC-3 cell, and a driver DNA or RNA is isolated from a cancer cell having low malignancy, e.g., an LNCaP cell.

In another embodiment, the tester DNA molecule is a double-stranded cDNA molecule and/or the driver DNA molecule is a double-stranded cDNA molecule.

In yet another embodiment, the amplification tag includes a double-stranded oligodeoxynucleotide sequence, preferably the AluI/SacI linker which includes the nucleic acid sequences shown in SEQ ID NO:6 and SEQ ID NO:7.

In a preferred embodiment, the reaction mixture is treated with a DNA nuclease which digests single-stranded DNA molecules. Preferably, the DNA nuclease is selected from the group consisting of mung bean nuclease, exonuclease VII, S1 nuclease, nuclease BAL-31 and nuclease P1.

In another embodiment, the hybridization step (b) occurs in the presence of an excess of the driver DNA or RNA molecule. Preferably, the steps (c) and (d) occur simultaneously.

In preferred embodiments, the method further includes repeating steps (b) through (e) at least one additional time, more preferably three or more times. The method further includes the steps of inserting the amplification product into a vector and constructing a subtraction library.

In yet other preferred embodiments, the amplification product is enriched for the tester DNA about 10 fold per cycle which includes steps (b) through (e), more preferably about 25 fold per cycle which includes steps (b) through (e), yet more preferably about 50–75 fold, most preferably 100 fold or more per cycle which includes steps (b) through (e).

Yet another aspect of the invention pertains to a method for identifying a difference between genomic DNA sequences. The method includes (a) providing a tester DNA molecule with an amplification tag at the 5' and 3' ends of the molecule and a driver DNA molecule lacking the amplification tag, (b) hybridizing the tester and the driver molecules to form a reaction mixture, wherein the reaction mixture comprises a tester—tester homoduplex, a tester-driver heteroduplex, a driver—driver homoduplex, a single-stranded driver DNA molecule and a single-stranded tester DNA molecule, (c) treating the reaction mixture to reduce the number of single-stranded molecules in the mixture and to remove the amplification tag from the tester-driver heteroduplex, and (d) amplifying the tester—tester homoduplex from the reaction mixture to form an amplification product, wherein step (c) occurs before step (d).

In one embodiment, the method further includes repeating steps (b) through (d) at least one additional time. In a preferred embodiment, the steps (b) through (d) are repeated three or more times. The method further includes the steps of inserting the amplification product into a vector and constructing a subtraction library.

In another embodiment, the amplification product is enriched for the tester DNA about 10 fold per cycle which includes steps (b) through (d), more preferably about 25 fold per cycle which includes steps (b) through (d), yet more preferably about 50–75 fold, most 100 fold or more per cycle which includes steps (b) through (d).

In another aspect, the invention features, a method for identifying a differentially expressed gene including (a) providing a tester DNA molecule with an amplification tag at the 5' and 3' ends of the molecule and a driver DNA or RNA molecule lacking the amplification tag, (b) hybridizing the tester and the driver molecules to form a reaction mixture, wherein the reaction mixture comprises a tester—tester homoduplex, a tester-driver heteroduplex, a driver—driver homoduplex, a single-stranded driver DNA molecule and a single-stranded tester DNA molecule, (c) treating the reaction mixture with a DNA nuclease which digests single-stranded DNA molecules to reduce the number of the single stranded molecules in the mixture and to remove the amplification tag from the tester-driver heteroduplexes, and (d) amplifying a tester—tester homoduplex from the reaction mixture to form an amplification product, wherein step (c) occurs before step (d).

In one embodiment, the tester DNA molecule is isolated from a cell which is exposed to conditions in vivo or in vitro which alter gene expression, e.g., a cancer cell, a virally infected cell, a cell exposed to selected chemical substances, a cell exposed to radiation, a cell exposed to different nutrient conditions, a cell exposed to selected factors (e.g., hormone or growth factors), and the driver DNA molecule is isolated from a normal cell. Similarly, the tester DNA molecule is isolated from a highly malignant cancer cell, e.g., a PC-3 cell, and a driver DNA or RNA is isolated from a cancer cell having low malignancy, e.g., an LNCaP cell.

In another embodiment, the tester DNA molecule is a double-stranded cDNA molecule and/or the driver DNA molecule is a double-stranded cDNA molecule.

In yet another embodiment, the amplification tag includes a double-stranded oligodeoxynucleotide sequence, preferably the AluI/SacI linker which includes the nucleic acid sequences shown in SEQ ID NO:6 and SEQ ID NO:7.

In a preferred embodiment, the reaction mixture is treated with a DNA nuclease which digests single-stranded DNA molecules. Preferably, the DNA nuclease is selected from the group consisting of mung bean nuclease, exonuclease VII, S1 nuclease, nuclease BAL-31 and nuclease P1.

In a preferred embodiment, the hybridization step (b) occurs in the presence of an excess of the driver DNA or RNA molecule.

In preferred embodiments, the method further includes repeating steps (b) through (d) at least one additional time, more preferably three or more times. The method further includes the steps of inserting the amplification product into a vector and constructing a subtraction library.

In yet other embodiments, the amplification product is enriched for the tester DNA about 10 fold per cycle which includes steps (b) through (d), more preferably about 25 fold per cycle which includes steps (b) through (d), yet more preferably about 50–75 fold, most preferably 100 fold or more per cycle which includes steps (b) through (d).

In yet another aspect, the invention features a method for identifying a differentially expressed gene including (a) providing a tester DNA molecule with an amplification tag at both 5' and 3' ends of the molecule and a driver DNA or RNA molecule lacking the amplification tag, (b) hybridizing the tester and the driver molecules to form a reaction mixture, wherein the reaction mixture comprises a tester—tester homoduplex, a tester-driver heteroduplex, a driver—driver homoduplex, a single-stranded driver DNA molecule and a single-stranded tester DNA molecule, (c) treating the reaction mixture with a DNA nuclease which digests single-stranded DNA molecules to reduce the number of the single stranded molecules in the mixture and to remove the amplification tag from the tester-driver heteroduplexes, (d) amplifying the tester—tester homoduplex from the reaction mixture to form an amplification product, wherein step (c) occurs before step (d), and (e) repeating steps (b) through (d) at least one additional time.

In one embodiment, the tester DNA molecule is isolated from a cell which is exposed to conditions in vivo or in vitro which alter gene expression, e.g., a cancer cell, a virally infected cell, a cell exposed to selected chemical substances, a cell exposed to radiation, a cell exposed to different nutrient conditions, a cell exposed to selected factors (e.g., hormone or growth factors), and the driver DNA molecule is isolated from a normal cell. Similarly, the tester DNA molecule is isolated from a highly malignant cancer cell, e.g., a PC-3 cell, and a driver DNA or RNA is isolated from a cancer cell having low malignancy, e.g., an LNCaP cell.

In another embodiment, the tester DNA molecule is a double-stranded cDNA molecule and/or the driver DNA molecule is a double-stranded cDNA molecule.

In yet another embodiment, the amplification tag includes a double-stranded oligodeoxynucleotide sequence, preferably the AluI/SacI linker which includes the nucleic acid sequences shown in SEQ ID NO:6 and SEQ ID NO:7.

In a preferred embodiment, the reaction mixture is treated with a DNA nuclease which digests single-stranded DNA molecules. Preferably, the DNA nuclease is selected from the group consisting of mung bean nuclease, exonuclease VII, S1 nuclease, nuclease BAL-31 and nuclease P1.

In one embodiment, the hybridization step (b) occurs in the presence of an excess of the driver DNA or RNA molecule.

In another embodiment, the method further includes repeating steps (b) through (e) at least one, preferably three or more times. The method further includes the steps of inserting the amplification product into a vector and constructing a subtraction library.

In yet other preferred embodiments, the amplification product is enriched for the tester DNA about 10 fold per cycle which includes steps (b) through (e), more preferably about 25 fold per cycle which includes steps (b) through (e), yet more preferably about 50–75 fold, most preferably 100 fold or more per cycle which includes steps (b) through (e).

The invention also pertains to a method for constructing a subtraction library including a differentially expressed gene. The method includes (a) providing a tester DNA molecule with an amplification tag at both 5' and 3' ends of the molecule and a driver DNA or RNA molecule lacking the amplification tag, (b) hybridizing the tester and the driver molecules to form a reaction mixture, wherein the reaction mixture comprises a tester—tester homoduplex, a tester-driver heteroduplex, a driver—driver homoduplex, a single-stranded driver DNA molecule and a single-stranded tester DNA molecule, (c) treating the reaction mixture with a DNA nuclease which digests single-stranded DNA molecules to reduce the number of the single-stranded molecules in the mixture and to remove the amplification tag from the tester-driver heteroduplexes, (d) amplifying the tester—tester homoduplex from the reaction mixture to form an amplification product, wherein step (c) occurs before step (d), (e) repeating steps (b) through (d) at least one additional time, (f) inserting an amplification product from step (e) into a vector, and (g) constructing a subtraction library.

In a preferred embodiment, the method further includes the steps of isolating a differentially expressed nucleic acid from the subtraction library.

In another aspect, the invention features a differentially expressed nucleic acid isolated by the method of the invention.

In preferred embodiments, the tester DNA molecule is isolated from a cell which is exposed to conditions in vivo or in vitro which alter gene expression, e.g., a cancer cell, a virally infected cell, a cell exposed to selected chemical substances, a cell exposed to radiation, a cell exposed to different nutrient conditions, a cell exposed to selected factors (e.g., hormone or growth factors), and the driver DNA molecule is isolated from a normal cell. Similarly, the tester DNA molecule is isolated from a highly malignant cancer cell, e.g., a PC-3 cell, and a driver DNA or RNA is isolated from a cancer cell having low malignancy, e.g., an LNCaP cell.

Yet another aspect of the invention pertains to a recombinant expression vector which includes the nucleic acid isolated by the method of the invention.

A still further aspect of the invention pertains to a cell, e.g., a host cell, containing a recombinant expression vector which includes the nucleic acid isolated by the method of the invention.

In another aspect, the invention features, a reaction mixture, preferably an in vitro reaction mixture, of the the method of the invention.

In one embodiment, the reaction mixture includes a tester—tester homoduplex, wherein the homoduplex includes an amplification tag at both 5' and 3' ends of the homoduplex molecule, a tester-driver heteroduplex lacking the amplification tags, and a driver—driver homoduplex lacking the amplification tags. The reaction mixture can further include one or more of the components of each step in the method of the invention.

In another embodiment, the reaction mixture further includes a DNA nuclease which digests single-stranded DNA molecules.

The invention also pertains to a kit for identifying a differentially expressed gene or for identifying a difference between genomic nucleic acid sequences.

In one embodiment, the kit includes an amplification tag, wherein the tag is a double-stranded oligodeoxynucleotide sequence having one restriction enzyme site, preferably having two restriction enzyme sites, and a DNA nuclease which digests single-stranded DNA molecules.

DETAILED DESCRIPTION OF THE INVENTION

Figure 1:
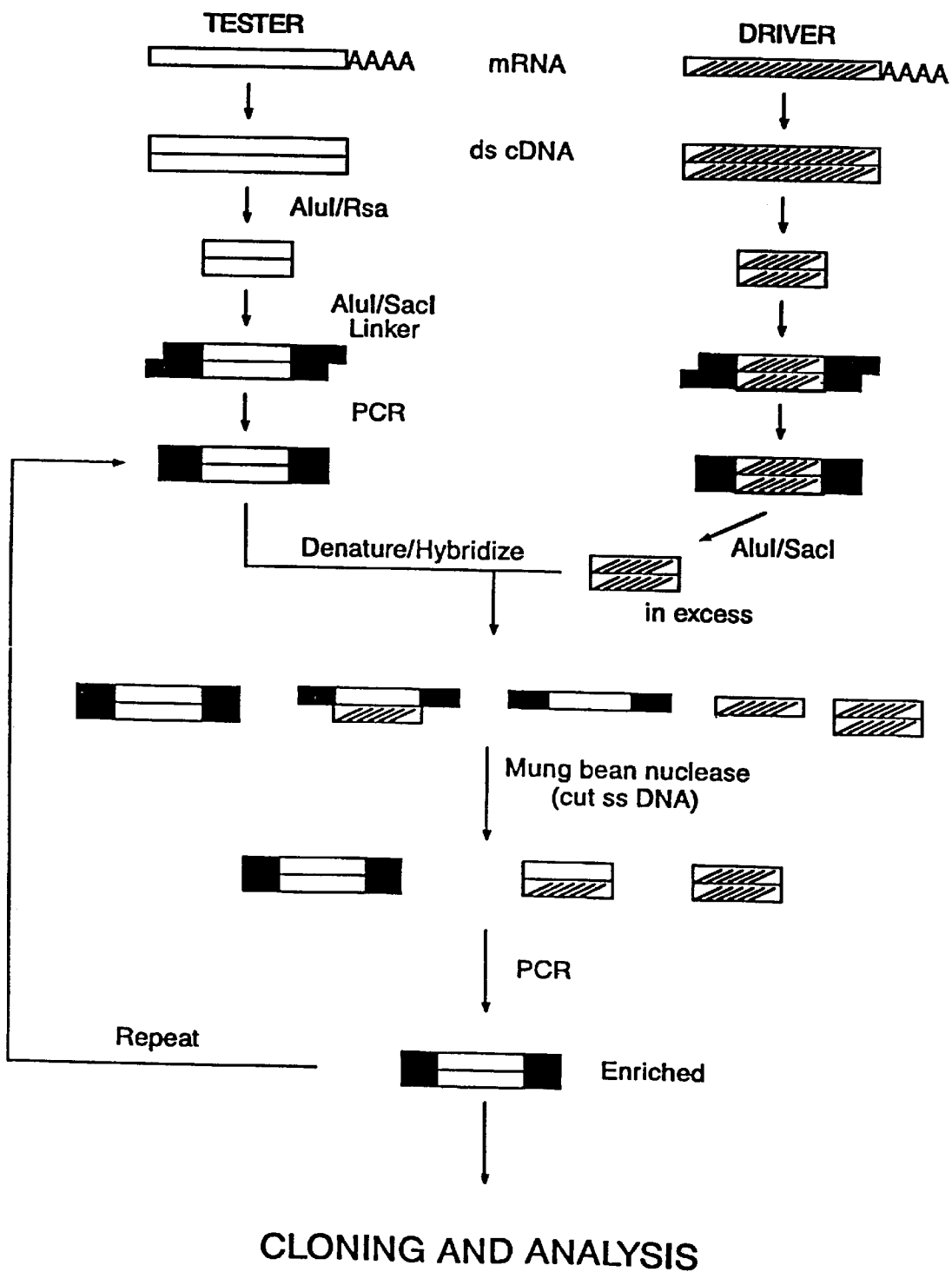
FIGURE 1 is a schematic diagram of the Linker Capture Subtraction method for identifying differentially expressed genes and differences in genomic nucleic acid sequences.

The present invention features a methods for identifying a differentially expressed gene or differences in genomic nucleic acid sequences. The method includes (a) providing a tester DNA molecule with an amplification tag at the 5' and 3' ends of the molecule and a driver DNA or RNA molecule lacking the amplification tag, (b) hybridizing the tester and the driver molecules to form a reaction mixture, wherein the reaction mixture comprises a tester—tester homoduplex, a tester-driver heteroduplex, a driver—driver homoduplex, a single-stranded driver DNA molecule and a single stranded tester DNA molecule, (c) treating the reaction mixture to reduce the number of single-stranded molecules in the mixture, (d) treating the reaction mixture to remove the amplification tag from the tester-driver heteroduplex, and (e) amplifying the tester—tester homoduplex from the reaction mixture to form an amplification product, wherein steps (c) and (d) occur before step (e). In one embodiment, steps (c) and (d) occur simultaneously. In another embodiment, steps (b) to (e) are repeated at least once and preferably at least three times.

As used herein, the term "differentially expressed gene" is an art-recognized term and includes, for example, a gene which is expressed in one cell type but not in another cell type, e.g., a gene which is preferentially expressed in a given cell type such as a cancer cell, but not in another cell type, for example, a normal cell, or a gene which is expressed at different levels in different cells of the same cell type.

The terms "tester DNA molecule" and "driver DNA molecule" refer to nucleic acid molecules, e.g., deoxyribonucleic acid molecules, single-stranded DNA molecules, double-stranded cDNA molecules, or genomic DNA molecules. Tester and driver DNA molecules are typically isolated from different sources, e.g., two different types of cells, such as a normal cell and a cancer cell, a highly malignant cell and a low malignant cell, the same cell type from two different organisms, e.g., different organisms within the same species or different organisms from different species, or two cells incubated or exposed to different conditions, e.g., incubated in vitro in the presence or absence of one or more of the following of, for example, cytokines, growth factors, or other biologically active molecules, or exposed to different environmental or stress conditions, e.g., UV, heat, or chemicals such as drugs. The term "driver RNA molecule" refers to a nucleic acid molecule, e.g., a ribonucleic acid molecule, preferably, an mRNA molecule. The driver RNA molecule can be isolated from the sources described herein for the tester and driver DNA molecules.

The amplification tags or linkers used in the methods of the invention refer to double-stranded oligonucleotide sequences, e.g., double-stranded oligodeoxynucleotide sequences, between about 15 to about 30 nucleotides in length, more preferably between about 20 to about 25 or more nucleotides in length. Preferably, the amplification tags include a first and a second oligonucleotide sequence wherein the first oligonucleotide sequence has a blunt 5' end and the second oligonucleotide sequence has a two base protruding 3' end and is phosphorylated at the 5' end. In other preferred embodiments, the amplification tags include at least one, preferably two, restriction enzyme sites near the 5' end. For example, the amplification tags can include an AluI/SacI site and/or another restriction enzyme site known to those skilled in the art. An example of an amplification tag which can be used in the method of the invention is a double stranded DNA molecule which includes the nucleic acid sequences shown in SEQ ID NO:6 and SEQ ID NO:7.

The tester and driver nucleic acid molecules are hybridized using standard techniques to form a reaction mixture which includes a tester—tester homoduplex, a tester-driver heteroduplex, a driver—driver homoduplex, a single-stranded driver DNA molecule and a single stranded tester DNA molecule. In one embodiment, the hybridization step occurs in the presence of excess driver nucleic acid molecules. Preferably, the driver nucleic acid molecules are present in about 25 fold excess per step, more preferably about 50 fold excess per step, most preferably about 75–100 fold or more excess per step. The term "duplex" refers to a double-stranded nucleic acid structure. Examples of duplexes include homoduplexes, e.g., tester—tester homoduplexes or driver—driver homoduplexes, or heteroduplexes, e.g., tester-driver heteroduplexes, as well as a duplex formed between a DNA and an RNA molecule. The reaction mixture is then treated, i.e., exposed to the appropriate conditions, to reduce the number of single-stranded molecules in the mixture and to remove the amplification tags from the tester-driver heteroduplex. In one embodiment, the reaction mixture is exposed to conditions, e.g., chemicals or enzymes, which can both reduce the number of single-stranded molecules in the mixture and remove the amplification tags, i.e., the single-stranded portions of double-stranded molecules, from the tester-driver heteroduplex. In a preferred embodiment, an enzyme, e.g., a DNA nuclease, capable of digesting single-stranded nucleic acid molecules is added to the reaction mixture. DNA nucleases which can be added to the reaction mixture include DNA nucleases which are known in the art and/or which are commercially available. Examples of DNA nucleases which can be used in the present invention include mung bean nuclease, exonuclease VII, S1 nuclease, nuclease BAL-31 and nuclease P1.

After the reaction mixture is treated to reduce the number of single-stranded molecules in the mixture and to remove the amplification tags, i.e., the single-stranded portions of double-stranded molecules, from the tester-driver heteroduplex, the tester—tester homoduplexes are amplified to form an amplification product. As used herein, the term "amplify" refers to any method which can be used to generate multiple copies of a nucleic acid, e.g., a DNA duplex or single-stranded DNA molecule, its complement, or both. Amplification techniques, therefore, include both cloning techniques, as well as PCR based amplification techniques. These techniques are well known to those of skill in the art. Amplification products are compositions which include a number of tester nucleic acid molecules having a sequence of interest which is greater than the number of tester nucleic acid molecules having the sequence of interest in the starting tester nucleic acid molecules. Preferably, the number of sequences of interest in the amplification product is increased about 10 fold over the starting number of sequences of interest, more preferably at least about 25 fold, yet more preferably at least about 50–75 fold, most preferably 100 fold or more, using the method of the invention.

The amplification product can be inserted into a vector and the vectors can be used to construct a subtraction library. Methods of inserting selected nucleic acid sequences into vectors and constructing libraries are known in the art (see, e.g., *Molecular Cloning: A Laboratory Manual,* 2nd Ed., ed. by Sambrook, Fritsch and Maniatis (Cold Spring Harbor Laboratory Press: 1989)) and described herein.

The invention also features differentially expressed nucleic acids, e.g., differentially expressed genes, isolated according to the methods of the invention. For example, the methods of the invention can be used to generate a subtraction library from which differentially expressed nucleic acids can be isolated. As described herein, at least five novel genes were identified and isolated according to the method of the invention. Partial sequences of three of these novel genes are set forth in the sequence listing as SEQ ID NOs:1–5.

The differentially expressed nucleic acids isolated according to the methods of the invention can be inserted into recombinant expression vectors using standard techniques. The recombinant expression vectors can then be introduced into a cell, e.g., a host cell. As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double-stranded DNA loops which, in their vector form are not bound to the chromosome. Another example of a commonly used vector is a viral vector.

"Cells," and "host cells" are terms used interchangeably herein. Cells or host cells of the invention include cells into which the nucleic acids isolated according to the method of the invention can be inserted. The cells can be prokaryotic or eukaryotic, e.g., mammalian, cells. Such terms refer not only to the particular subject cell, i.e., a selected cell into which the nucleic acid isolated according to the invention is introduced, but to the progeny or potential progeny of such a cell.

Novel differentially expressed genes isolated by the method of the invention, e.g., SEQ ID NOs: 1–5, can also be used as a part of a gene therapy protocol to deliver nucleic acids encoding either an agonistic or antagonistic form of a novel polypeptide. As used herein, the phrase "gene therapy" refers to the transfer of genetic material (e.g., differentially expressed nucleic acid isolated as described herein) of interest into a host to reconstitute the function of, enhance the function of, or alternatively, antagonize the function of a novel polypeptide in a cell in which the polypeptide is expressed or misexpressed. The genetic material of interest encodes a product (e.g., a protein polypeptide, peptide or functional RNA) whose production in vivo is desired.

Expression constructs of a novel polypeptide encoded by a nucleic acid isolated by the method of the invention, can be administered in any biologically effective carrier, e.g. any formulation or composition capable of effectively delivering the novel gene to cells in vivo. Methods of producing such expression vectors include insertion of the subject gene into viral vectors including recombinant retroviruses, adenovirus, adeno-associated virus, and herpes simplex virus-1, or recombinant bacterial or eukaryotic plasmids. Viral vectors can transfect cells directly while plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA encoding a novel polypeptide isolated by the method of the invention. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψ Am. Retroviruses have been used to introduce a variety of genes into many different cell types, including epithelial cells, in vitro and/or in vivo (see, e.g., Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad Sci. USA* 85:3014–3018; Armentano et al. (1990) *Proc. Natl. Acad Sci. USA* 87:6141–6145; Huber et al. (1991) *Proc. Natl. Acad. Sci. USA* 88:8039–8043; Ferry et al. (1991) *Proc. Natl. Acad Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, e.g., Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of a novel gene isolated by the method of the invention is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) *Curr. Topics in Micro. and Immunol.* 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of a novel polypeptide encoded by a nucleic acid isolated by the method of the invention in the tissue of a mammal, such as a human. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of a novel gene isolated by the method of the invention by the targeted cell. Exemplary gene delivery systems of this type include liposomal derived systems, polylysine conjugates, and artificial viral envelopes.

In a representative embodiment, a gene isolated by the method of the invention can be entrapped in liposomes bearing positive charges on their surface (e.g., lipofectins) and (optionally) which are tagged with antibodies against cell surface antigens of the target tissue (Mizuno et al.

(1992) *No Shinkei Geka* 20:547–551; PCT publication WO91/06309; Japanese patent application 1047381; and European patent publication EP-A-43075).

In clinical settings, the gene delivery systems for the therapeutic differentially expressed gene can be introduced into a patient by any of a number of methods, each of which is known in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *Proc. Natl. Acad. Sci USA* 91: 3054–3057).

The pharmaceutical preparation of the gene therapy construct can include the gene delivery system in an acceptable carrier or diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

In another aspect, the invention features a reaction mixture, preferably an in vitro reaction mixture, used in a method of the invention. In a preferred embodiment, the reaction mixture includes a tester—tester homoduplex, wherein the homoduplex includes an amplification tag at both 5' and 3' ends of the homoduplex molecule, a tester-driver heteroduplex lacking the amplification tags, and a driver—driver homoduplex lacking said amplification tags. In other preferred embodiments, the reaction mixture further includes a tester-driver heteroduplex, wherein the heteroduplex includes an amplification tag at both 5' and 3' ends of the heteroduplex molecule, and/or a DNA nuclease which digests single-stranded DNA molecules.

In yet another aspect, the invention features a kit for identifying a differentially expressed gene or for identifying a difference between genomic nucleic acid sequences. In a preferred embodiment, the kit includes an amplification tag/linker, wherein the tag/linker is a double-stranded oligodeoxynucleotide sequence having one restriction enzyme site, preferably having two restriction enzyme sites, near the 5' end of the tag/linker, and a DNA nuclease which digests single-stranded DNA molecules. The kits of the invention typically include other components such as reagents for performing hybridization reactions and reagents for performing amplification reactions, e.g., PCR reagents. The kits of the invention can also include restriction enzymes, e.g., AluI, RsaI, and SacI, specific for the restriction enzyme sites in the double-stranded oligodeoxynucleotide tag/linker sequences as well as the appropriate buffers required for each step in the method of the invention, e.g., appropriate buffers, pH, salt conditions, for a DNA nuclease which digests single-stranded DNA molecules, e.g., mung bean nuclease. The kits of the invention can also include reagents for sample processing such as detergents, chaotropic salts and the like, immobilization means such as particles, supports, wells, dipsticks and the like, and labeling means such as dyes, developing reagents, radioisotopes, fluorescent agents, luminescent or chemiluminescent agents, enzymes, intercalating agents and the like. Kits of the invention can further include instructions for use.

The practice of the present invention employs, unless otherwise indicated, conventional techniques of cell biology, cell culture, molecular biology, transgenic biology, microbiology, recombinant DNA, and immunology, which are within the skill of the art. Such techniques are described in the literature. See, e.g, *Molecular Cloning: A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. : 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

There are several advantages of the method of the invention, designated LCS, over previous methods of identifying differentially expressed genes and differences between genomic nucleic acid sequences. First, LCS is highly effective. When LCS is employed, there is a strong stepwise enrichment of target sequences. An example of this enrichment is described in the Exemplification section. As described in the Exemplification section, when the PCR-amplified products of the third round of subtraction of the method of the invention were cloned, 81% of randomly picked clones (78 out of 96 colonies) corresponded to mRNAs expressed differentially between the cell lines compared, i.e., the LNCaP and PC-3 cell lines. Such a high efficiency has not been reported by others, and it obviates the need to screen the subtractive library by differential hybridization, an essential step in some other methods.

Secondly, LCS is straightforward to perform and contains fewer steps than other methods. In particular, a variety of labor intensive and potentially error-prone physical partitioning steps, such as biotinylation or repeated phenol extraction/ethanol precipitation, are eliminated in LCS. In LCS, all the steps of subtractive hybridization, mung bean nuclease digestion and PCR amplification can be performed in one PCR tube, which makes the process feasible for automation.

Thirdly, LCS is a fast and economical process. The materials required are kept to a minimum. The procedure, from isolation of mRNA to construction of the subtractive library, can be completed within one week.

Unlike RDA (Lisitsyn et al. (1993) *Science* 259:946–951) which uses a kinetic mechanism of enrichment, LCS achieves enrichment by specifically preserving PCR-priming sites (amplification tags/linkers) of target sequences. Enzymes which digest single-stranded nucleic acids, e.g., DNA nucleases such as mung bean nuclease, play a central role in the LCS. These nucleases remove amplification tags/linkers of all other tagged/linkered sequences except for tester—tester homoduplexes. The nucleases also digest single stranded DNA in the hybridization solution which is an abundant species that might otherwise cause high background or even failure of enrichment. The use of the enzyme is more reliable and efficient than other physical partitioning methods as indicated by the high enrichment of target sequences and efficient isolation of numerous differentially expressed genes in the experiments described in the Exemplification section. For example, exonuclease VII, also specific for single-stranded DNA, could be employed in the LCS protocol. Exonuclease VII has the added advantage of a pH optimum near to those of the subtractive hybridization and PCR reaction, thus eliminating the need for pH-shift buffers in the process.

The digestion of double stranded cDNA with different restriction enzymes gives a representation of the mRNA population. In the example of Linker Capture Subtraction described in the Exemplification section, Alu I and Rsa I were employed. The use of enzymes in addition to these two enzymes provide different representations and can result in the isolation of genes different from those achievable using Alu I and Rsa I. The use of different restriction enzymes is encompassed by the present invention. Also, the use of different PCR conditions such as additional concentrations of magnesium, different annealing temperatures, and the addition of reagents such as DMSO, formamide or glycerol achieve other representations of the mRNA population of the selected cells. Moreover, thermostable DNA polymerases from different vendors can also give different representations because these enzymes have different efficiencies in amplifying large-size fragments.

The same amplification tag/linker was added to the tester and driver in the experiment described herein. Addition of different amplification tags/linkers give an unequivalent representation of starting mRNAs for tester and driver, probably due to sequence-contexting of primers or so-called PCR "bias", a tendency to amplify some sequences preferentially. Therefore, it was found to be advantageous to use the same amplification tag/linker, for both tester and driver rather than different tags/linkers. The protocol outlined herein itself has a mechanism to eliminate the contamination problem of the residual linkered driver. Since the unlinkered driver is present at high excess in the reaction, the residual linkered driver is driven out by the unlinkered driver. Too high a level of linkered driver would still pose a problem for efficiency of enrichment. Therefore, a linker was designed with both Alu I and Sac I sites included to ensure maximum removal of linker sequences from driver. Incubation with Alu I first and then Sac I was used to avoid incorporation of driver DNA into the library, since the Sac I site was used for library construction.

How to achieve an enrichment for both abundant and rare target genes is always an issue for the methods of cloning differentially expressed genes. For LCS, the hybridization time is likely the determining factor. Short hybridization times favor enrichment of more abundant sequences, while longer times allow rare sequences to bind. As long as enough time is given for hybridization, rare target sequences can remain in the reaction. Indeed, moderate to rare genes are included in the genes identified by this method. Moreover, as noted by Hubank and Schatz (Hubank and Schatz (1994) *Nucleic Acids Res.* 22:5640–5648), unwanted dominant sequences (i.e., already identified sequences in the reaction) can be driven out by supplementing driver with unlinkered corresponding sequences. This allows less dominant species to be isolated. Tester and driver can also be normalized before subtraction. The following procedure can be used: First, both tester and driver are denatured and hybridized for a short time (e.g., one hour). Then, the linkers of duplexes/hybrids (more abundant sequences) are removed by restriction enzymes. Finally, the remaining single-stranded fraction of DNA is amplified by PCR. Proper sampling of target genes that differ in abundance by only a few-fold is another issue. By adjustment of the tester/driver ratios and by more cycles of subtraction, these genes can be isolated.

Accordingly, LCS is generally applicable to experiments such as those reported herein as well as to studies of differential gene expression in cells incubated in the absence or presence of cytokines, growth factors or other biologically active molecules; or for identification and/or isolation of genes expressed preferentially in a particular cell type, e.g., a cancer cell versus a normal cell. Moreover, the method of the present invention is also useful in finding differences between genomic DNAs or in isolation of target genes for gene therapy.

This invention is further illustrated by the following Exemplification which should not be construed as limiting. The contents of all references and published patents and patent applications cited throughout the application are hereby incorporated by reference.

EXEMPLIFICATION

Experimental Strategy

This method is designed to isolate genes expressed differentially between two cell types or between cells treated in two different ways or for isolation of differences between genomic DNA sequences (FIGURE 1). In the first step, both tester DNA and driver DNA are prepared. This is accomplished by digesting the double-stranded cDNA with restriction enzymes of choice, ligating the fragments to amplification tags, e.g., linkers, and carrying out a PCR reaction with linker sequence as primer. The driver DNA is digested with restriction enzymes to remove the linker sequence. In the second step, the tagged/linkered tester DNA is hybridized to an excess of driver DNA (with tags/linkers removed) followed by incubation with mung bean nuclease which digests single-stranded DNA specifically. This leaves only linkered tester—tester homohybrids and unlinkered homo- and heteroduplexes. In the following step, the linkered tester—tester homoduplexes are amplified by PCR with tag/linker sequence as primer to fulfill the first round of enrichment. The amplified PCR products are then used as tester for another round of subtraction. The process of subtractive hybridization, mung bean nuclease digestion, and PCR amplification is carried out three times. Finally, the PCR products of the third round of subtraction are used to prepare a subtraction library by inserting them into a vector.

THE FOLLOWING MATERIAL AND METHODS WERE USED IN THIS EXEMPLIFICATION

Cell culture and cDNA preparation

Human prostate cancer lines LNCaP and PC-3 cells (American Type Culture Collection, Rockville, Md.) were cultured in RPMI-1640 medium with 10% fetal bovine serum, 95% air/5% $CO_2$ at 37° C. Total RNA was isolated by a guanidinium thiocyanate/phenol method (Xie and Rothblum (1991) *BioTechniques* 11:325–327). Poly(A)$^+$ RNA was selected through oligo(dT)$_{25}$-Dynabeads (Dynal Inc., Lake Success, N.Y.). cDNA was synthesized from 2 µg of poly(A)$^+$ RNA using a SuperScript Choice System (GIBCO, Gaithersburg, Md.) according to the manufacturer's instruction. Oligo(dT)$_{12-18}$ was used to prime the first strand of cDNA synthesis.

Restriction Enzyme Digestion, linker ligation, and PCR amplification

The double-stranded cDNA was digested with Alu I and Rsa I, then ligated with a double-stranded oligodeoxynucleotide linker, which had a blunt end and a 2-base 3' protruding end:

ACTCTTGCTTGGACGAGCTCT (SEQ ID NO:6)

ACTGAGAACGAACCTGCTCGAGA-p (SEQ ID NO:7)

The linker contained an Alu I/Sac I site near the blunt end as indicated. The top strand was designated the amplification primer (AP). The bottom strand was phosphorylated at the 5' end. The linker was prepared by annealing the two strands. An equal mass of each of the two oligodeoxynucleotides was combined. The mixture was heated to 90° C. for 2 min, then allowed to cool to room temperature. The ligation was carried out by mixing 1 µg of cut cDNA, 5 µg of linker, 1×ligation buffer (Stratagene, La Jolla, Calif.) and 4 Weiss units of T4 DNA Ligase (Stratagene) in a volume of 10 µl at 8° C., 20 hours. The reaction mixture was electrophoresed through a 2% low-melt agarose gel to remove the unligated linkers. The linker-ligated cDNA fragments in the size range of 0.1–1.0 kb were collected.

Linker-ligated cDNA fragments in agarose were amplified directly by PCR using AP as primer. The reaction (100 µl) contained 10 mM Tris-HCl, pH 8.9, 50 mM KCl, 0.1% Triton X-100, 200 µM dNTPs, 1 µM AP, 2 mM $MgCl_2$, 1 µl of melted agarose, and 5 U of Taq polymerase (Promega), running for 30 cycles (94° C., 1 min; 55° C., 1 min; 72° C., 1 min). The amplified cDNA fragments were purified using a Gene-Clean kit (Bio101, Vista, Calif.) and were used as the initial material for subtractive hybridization.

Subtractive Hybridization

Twenty micrograms of PCR-amplified driver DNA were digested with Alu I (50 U), 37° C., 2 hr, followed by Sac I (50 U), 1 hr to cleave the linker so that driver DNA could not be amplified later. After digestion, the products were purified using Gene-Clean.

The digested driver DNA (2.5 µg) and nondigested tester DNA (0.1 µg) were mixed, vacuum-dried and redissolved in 4 µl of a buffer containing 15 mM N-(2-hydroxy ethyl) piperazine-N'-(3-propane sulfonic acid) (EPPS), pH 8.0/1.5 mM EDTA, overlaid with mineral oil, and denatured by heating for 5 min at 100° C. One µl of 5M NaCl was added, and the DNA was hybridized for 20 hr at 67° C. After hybridization, 20 µl of pH-shift buffer A (1 mM $ZnCl_2$, 10 mM Na acetate, pH 5.0) was added and the solution was divided into 5 aliquots. The aliquots were incubated with 0, 0.85, 1.75, 3.5, or 7 U of mung bean nuclease (Promega), respectively, 37° C. for 30 min. To each sample was added 80 µl of pH-shift buffer B (10 mM Tris-HCl, pH 8.9, 50 mM KCl, and 0.1% Triton X-100). They were heated (95° C., 5 min) to inactivate the mung bean nuclease. Then 20 µl of enzyme solution (10 mM Tris-HCl, pH 8.9, 50 mM KCl, and 0.1% Triton X-100, 1 mM dNTPs, 5 µM AP, 10 mM $MgCl_2$ and 5 U of Taq polymerase (Promega)) was added. The PCR reaction was run under the same conditions as above. Each sample was electrophoresed on 2% agarose gel. The sample with the most abundant products of 0.1–1.0 kb was selected as tester for another round of subtraction. The above process was repeated twice with 2.5 µg of driver DNA and 0.025 µg of tester DNA. To test for enrichment of target sequences, PCR products derived from subtraction cycles 0–3 were electrophoresed on 4% NuSieve agarose (FMC, Rockland, Me.), transferred to GeneScreen Plus membrane (Dupont/NEN, Boston, Mass.) and probed with the random-labeled PCR products (with linkers removed) of the third round of subtraction.

Construction of subtractive library and clonal analysis

After three rounds of subtraction, the PCR-amplified products were purified (Gene Clean, BIO 101, La Jolla, Calif.), digested with Sac I, inserted into dephosphorylated pGEM-7Zf (+) (Promega) at the Sac I site and transformed into competent E. coli JM109 cells. Two subtractive libraries were prepared in this way: LNCaP (tester)/PC-3 (driver)= "L-P", and PC-3 (tester)/LNCaP (driver)="P-L".

Forty eight white colonies from each library were picked randomly and inoculated into LB+Amp medium in individual wells of a 96-well plate. Two replica DNA dot-blots were prepared on GeneScreen Plus filters using 25 µl of bacterial cells per well. The replica dot-blots were processed according to Brown and Knudson ((1991) BioTechniques 10:719–722) and probed with random-labeled driver DNAs from LNCaP and PC-3, respectively.

Candidate positive colonies were boiled for 5 min in 20 µl $H_2O$ and centrifuged. DNA in the supernatant was amplified by PCR using universal vector primer T7 and SP6 for 20 cycles of 94° C., 1 min; 55° C., 1 min; 72° C., 1 min. The PCR products were electrophoresed on 2% agarose. The desired bands were excised and purified (Gene Clean). The products were subjected to direct DNA sequencing (Brown and Knudson (1991) BioTechniques 10:719–722), and were employed as probes in Northern blot analyses.

Cloning and analysis of differentially expressed genes between the human prostate cancer cell lines LNCaP and PC-3

The strategy outlined above was used to begin to clone and identify the genes expressed differentially between the human prostate cancer cell lines LNCaP and PC-3, which have different tumorigenic and metastatic potentials. After three cycles of subtraction, the PCR products were cleaved with Sac I, inserted into pGEM-7Zf(+) and transformed into E. coli JM109 cells. The PCR-amplified DNA derived from subtraction cycles 0–3 was electrophoretically analyzed. 10 µl of PCR reaction mixture were electrophoresed on 4% NuSieve agarose gel. The original unsubtracted DNAs from LNCaP and PC-3 moved as a smear between 0.1–1.0 Kb. As subtraction rounds were performed, distinct bands were seen. The intensity and resolution of these bands increased progressively with successive subtraction. When labeled PCR products of the third round of subtraction were electrophoresed on a 6% sequencing gel, 50–60 bands could be seen. DNA of the agarose gel was transferred to Gene Screen Plus membrane, and probed with the labeled PCR products of the third round of subtraction L-P, 3 or P-L, 3. The results indicated strong enrichment of differentially expressed sequences.

After three rounds of subtraction, the PCR-amplified products were inserted into pGEM-7Zf(+) and transformed into E. coli JM109 cells. 48 white colonies were randomly picked from each of the libraries and grown in LB medium in individual wells of a 96-well plate. Two replica DNA dot-blots were prepared and probed with the labeled driver DNAs from LNCaP and PC-3, respectively. A comparison of the hybridization intensity of a clone in two replica membranes revealed the relative abundance of the transcript in the two cell types. Over two-thirds of the selected clones demonstrated significant differences in abundance. Clones were tested further by Northern blot. Briefly, 5 µg of total RNA from LNCaP or PC-3 cells was electrophoresed in a 1% agarose/formaldehyde gel, transferred to a GeneScreen Plus membrane and probed with the $^{32}P$ random labelled PCR products. The results of the Northern blot are shown below in Table I.

TABLE I

TISSUE EXPRESSION

| CLONE | A | B | C | D | E | F | G | H | I | J | K | L | M | N | O | P |
|---|---|---|---|---|---|---|---|---|---|---|---|---|---|---|---|---|
| P1 (SEQ ID NO:1) | + | − | +++ | − | +++ | ++ | + | ++ | ++ | − | ++ | + | ++ | + | + | + |
| P2 (SEQ ID NO:2) | − | − | ++ | − | − | ++ | + | − | − | − | − | − | − | − | − | + |
| P3 (SEQ ID NO:3) | − | + | + | + | ++ | ++ | ++ | − | +++ | +++ | ++ | + | − | + | ++ | +++ |

Codes used in Table I:
1. "−" = no detectable expression in a given tissue;
"+" = expression in a given tissue
2. A = spleen;
B = thymus;
C = prostate;
D = testis;
E = ovary;
F = small intestine;
G = colon (mucosal lining);
H = peripheral blood leukocytes;
I = heart;
J = brain;
K = placenta;
L = lung;
M = liver;
N = skeletal muscle;
O = kidney; and
P = pancreas The clones were then sequenced by direct DNA sequencing. Specifically, the amplified DNA fragments were isolated by agarose gel electrophoresis and purified using Gene-Clean kit. The DNA was sequenced with the same primer used for amplification by the direct sequencing procedure from the "Sequenase" protocol (United States Biochemical Corp., Cleveland, Ohio) as modified by Winship ((1989) Nucleic Acids Res. 17:1266).

From 78 colonies, 15 distinct clones were identified which correspond to mRNAs expressed differentially between LNCaP and PC-3 cell lines. The extent of differential expression ranged from several fold to greater than 100 fold. Using the method of the invention, five novel genes were identified as well as other known genes which are or may be involved in signal transduction, tumor growth, tumor invasion and metastasis. A Northern blot exemplifying differential expression of two genes was performed. Total RNA from LNCAP and PC-3 cells was electrophoresed and probed with radiolabeled cDNA of two differentially expressed clones isolated by LCS. DNA sequence analyses demonstrated that the LNCaP specific gene is prostate specific antigen (PSA) which is known to be expressed in LNCaP but not in PC-3 (Winship (1989) Nucleic Acids Res. 17:1266). The PC-3 specific gene was found to be vimentin, the differential expression of which has not been reported previously in these prostate cancer cells.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

We claim:

1. A method for identifying a differentially expressed gene, comprising:
   (a) providing a tester DNA molecule with an amplification tag at the 5' and 3' ends of the molecule and a driver DNA or RNA molecule lacking said amplification tag;
   (b) hybridizing said tester and said driver molecules to form a reaction mixture, wherein said reaction mixture comprises a tester—tester homoduplex, a tester-driver heteroduplex, a driver—driver homoduplex, a single stranded driver DNA molecule and a single stranded tester DNA molecule;
   (c) treating said reaction mixture to reduce the number of single stranded molecules in said mixture;
   (d) treating said reaction mixture to remove said amplification tag from said tester-driver heteroduplex; and
   (e) amplifying said tester—tester homoduplex from said reaction mixture to form an amplification product, wherein steps (c) and (d) occur before step (e).

2. The method of claim 1 wherein said tester DNA molecule is isolated from a cancer cell.

3. The method of claim 1 wherein said driver DNA molecule is isolated from a normal cell.

4. The method of claim 1 wherein said tester DNA molecule is a double stranded cDNA molecule.

5. The method of claim 1 wherein said driver DNA molecule is a double stranded cDNA molecule.

6. The method of claim 1 wherein said amplification tag comprises a double stranded oligodeoxynucleotide sequence.

7. The method of claim 6 wherein said double stranded oligodeoxynucleotide sequence is the AluI/SacI linker which comprises the nucleic acid sequences shown in SEQ ID NO:6 and SEQ ID NO:7.

8. The method of claim 1 wherein said steps (c) and (d) occur simultaneously.

9. The method of claim 1 wherein said hybridization step (b) occurs in the presence of an excess of said driver DNA molecule.

10. The method of claim 1 wherein said reaction mixture is treated with a DNA nuclease which digests single stranded DNA molecules.

11. The method of claim 1 wherein said DNA nuclease is selected from the group consisting of mung bean nuclease, exonuclease VII, S1 nuclease, nuclease BAL-31 and nuclease P1.

12. The method of claim 1 wherein said method further comprises repeating steps (b) through (e) at least one additional time.

13. The method of claim 1 wherein said method further comprises the steps of inserting said amplification product into a vector and constructing a subtraction library.

14. A method for identifying a differentially expressed gene, comprising:
   (a) providing a tester DNA molecule with an amplification tag at the 5' and 3' ends of the molecule and a driver DNA or RNA molecule lacking said amplification tag;
   (b) hybridizing said tester and said driver molecules to form a reaction mixture, wherein said reaction mixture comprises a tester—tester homoduplex, a tester-driver heteroduplex, a driver—driver homoduplex, a single stranded driver DNA molecule and a single stranded tester DNA molecule;

(c) treating said reaction mixture with a DNA nuclease which digests single stranded DNA molecules to reduce the number of said single stranded molecules in said mixture and to remove said amplification tag from said tester-driver heteroduplexes; and (d) amplifying said tester—tester homoduplex from said reaction mixture to form an amplification product, wherein step (c) occurs before step (d).

15. The method of claim 14 wherein said tester DNA molecule is isolated from a cancer cell.

16. The method of claim 14 wherein said driver DNA molecule is isolated from a normal cell.

17. The method of claim 14 wherein said tester DNA molecule is a double stranded cDNA molecule.

18. The method of claim 14 wherein said driver DNA molecule is a double stranded cDNA molecule.

19. The method of claim 14 wherein said amplification tag comprises a double stranded oligodeoxynucleotide sequence.

20. The method of claim 19 wherein said double stranded oligodeoxynucleotide sequence is the AluI/SacI linker which comprises the nucleic acid sequences shown in SEQ ID NO:6 and SEQ ID NO:7.

21. The method of claim 14 wherein said hybridization step (b) occurs in the presence of an excess of said driver DNA molecule.

22. The method of claim 14 wherein said DNA nuclease is selected from the group consisting of mung bean nuclease, exonuclease VII, S1 nuclease, nuclease BAL-31 and nuclease P1.

23. The method of claim 14 wherein said method further comprises repeating steps (b) through (d) at least one additional time.

24. The method of claim 14 wherein said method further comprises the steps of inserting said amplification product into a vector and constructing a subtraction library.

25. A method for constructing a subtraction library containing a differentially expressed gene, comprising:

(a) providing a tester DNA molecule with an amplification tag at both 5' and 3' ends of the molecule and a driver DNA or RNA molecule lacking said amplification tag;

(b) hybridizing said tester and said driver molecules to form a reaction mixture, wherein said reaction mixture comprises a tester—tester homoduplex, a tester-driver heteroduplex, a driver—driver homoduplex, a single stranded driver DNA molecule and a single stranded tester DNA molecule;

(c) treating said reaction mixture with a DNA nuclease which digests single stranded DNA molecules to reduce the number of said single stranded molecules in said mixture and to remove said amplification tag from said tester-driver heteroduplexes;

(d) amplifying said tester—tester homoduplex from said reaction mixture to form an amplification product, wherein step (c) occurs before step (d);

(e) repeating steps (b) through (d) at least one additional time;

(f) inserting an amplification product from step (e) into a vector; and (g) constructing a subtraction library.

26. The method of claim 25 wherein said method further comprises the steps of isolating a differentially expressed nucleic acid from said subtraction library.

27. A differentially expressed nucleic acid isolated by the method of claim 26.

28. The nucleic acid of claim 27 wherein said nucleic acid is isolated from a cancer cell.

29. A recombinant expression vector comprising the nucleic acid of claim 27.

30. A cell comprising the recombinant expression vector of claim 29.

31. A reaction mixture comprising a tester—tester homoduplex, wherein said homoduplex includes an amplification tag at both 5' and 3' ends of the homoduplex molecule, a tester-driver heteroduplex lacking the amplification tags, and a driver—driver homoduplex lacking the amplification tags.

32. The reaction mixture of claim 31 further comprising a DNA nuclease which digests single stranded DNA molecules.

33. A method for identifying a difference between genomic DNA sequences, comprising:

(a) providing a tester DNA molecule with an amplification tag at the 5' and 3' ends of the molecule and a driver DNA molecule lacking said amplification tag;

(b) hybridizing said tester and said driver molecules to form a reaction mixture, wherein said reaction mixture comprises a tester—tester homoduplex, a tester-driver heteroduplex, a driver—driver homoduplex, a single stranded driver DNA molecule and a single stranded tester DNA molecule;

(c) treating said reaction mixture to reduce the number of single stranded molecules in the mixture and to remove said amplification tag from the tester-driver heteroduplex; and (d) amplifying said tester—tester homoduplex from said reaction mixture to form an amplification product, wherein step (c) occurs before step (d).

34. A kit comprising an amplification tag, wherein said tag is a double-stranded oligodeoxynucleotide sequence having two restriction enzyme sites, and a DNA nuclease which digests single-stranded DNA molecules.

* * * * *

UNITED STATES PATENT AND TRADEMARK OFFICE
CERTIFICATE OF CORRECTION

PATENT NO.   : 5,804,382
DATED        : September 8, 1998
INVENTOR(S)  : Arthur J. Sytkowki and Meiheng Yang It is certified that error appears in the above-identified patent and that said Letters Patent is hereby corrected as shown below:

At column 1, line 5 - please insert:

--This invention was made with Government support under NIH grant 1F32DK09364 and DK38841 and U.S. Navy grant N00014-93-1-0076. The Government has certain rights in the invention.--

Signed and Sealed this

Eighth Day of June, 1999

Attest:

Q. TODD DICKINSON

*Attesting Officer*   *Acting Commissioner of Patents and Trademarks*